United States Patent [19]
Noble et al.

[11] Patent Number: 5,665,091
[45] Date of Patent: Sep. 9, 1997

[54] SURGICAL BROACH

[75] Inventors: Philip C. Noble, Houston, Tex.;
Michael A. Hammer, Kenilworth, N.J.;
Glen A. Kashuba, River Edge, N.J.;
Steven J. Sawicki, Lake Hopatcong, N.J.; Ben J. Verhoog, North Haledon, N.J.; Richard G. Eckrote, Lincoln Park, N.J.

[73] Assignee: Howmedica Inc., New York, N.Y.

[21] Appl. No.: 594,892

[22] Filed: Feb. 9, 1996

[51] Int. Cl.$^6$ .................................................. A61B 17/88
[52] U.S. Cl. .................................................. 606/85; 606/79
[58] Field of Search ................. 606/80, 81, 82, 606/84, 85, 99; 623/18, 23

[56] References Cited

U.S. PATENT DOCUMENTS

| | | |
|---|---|---|
| 4,552,136 | 11/1985 | Kenna . |
| 4,601,289 | 7/1986 | Chiarizzio et al. . |
| 4,625,725 | 12/1986 | Davison et al. .............. 606/85 |
| 4,765,328 | 8/1988 | Keller et al. . |
| 5,006,121 | 4/1991 | Hafeli . |
| 5,019,082 | 5/1991 | Frey et al. . |
| 5,041,118 | 8/1991 | Wasilewski . |
| 5,062,854 | 11/1991 | Noble et al. .............. 623/23 |
| 5,089,004 | 2/1992 | Averill et al. . |
| 5,342,365 | 8/1994 | Waldman . |
| 5,454,815 | 10/1995 | Geisser et al. . |

OTHER PUBLICATIONS

Alexander, J.W., Miller, L.R., Noble, P.C., Kamaric, E., "Machining Characteristics of Femoral Broaches with Different Cutting Tooth Designs," presented at the 21st Annual Meeting of the Society for Biomaterials, Mar. 18–22, 1995, San Francisco, CA, USA.

Zimmer catalog—"SixTi28™ Total Hip Prosthesis" (3 pages, including enlarged view); date—pre-1995.

Zimmer Package Insert—"SixTI/32™ Total Hip Replacement" (1 page); date—Nov. 1980.

*Primary Examiner*—Michael Buiz
*Assistant Examiner*—David O. Reip
*Attorney, Agent, or Firm*—Peter C. Richardson; Raymond W. Augustin; Laura G. Barrow

[57] ABSTRACT

An improved surgical broach for preparing an intramedullary canal of a bone for receiving a prosthesis is described, wherein the broach comprises a plurality of cutting teeth having different configurations and placement upon the broach for optimizing cutting efficiency and speed for improved surgical ease-of-use while minimizing gap formation between the prosthesis and the intramedullary canal.

29 Claims, 14 Drawing Sheets

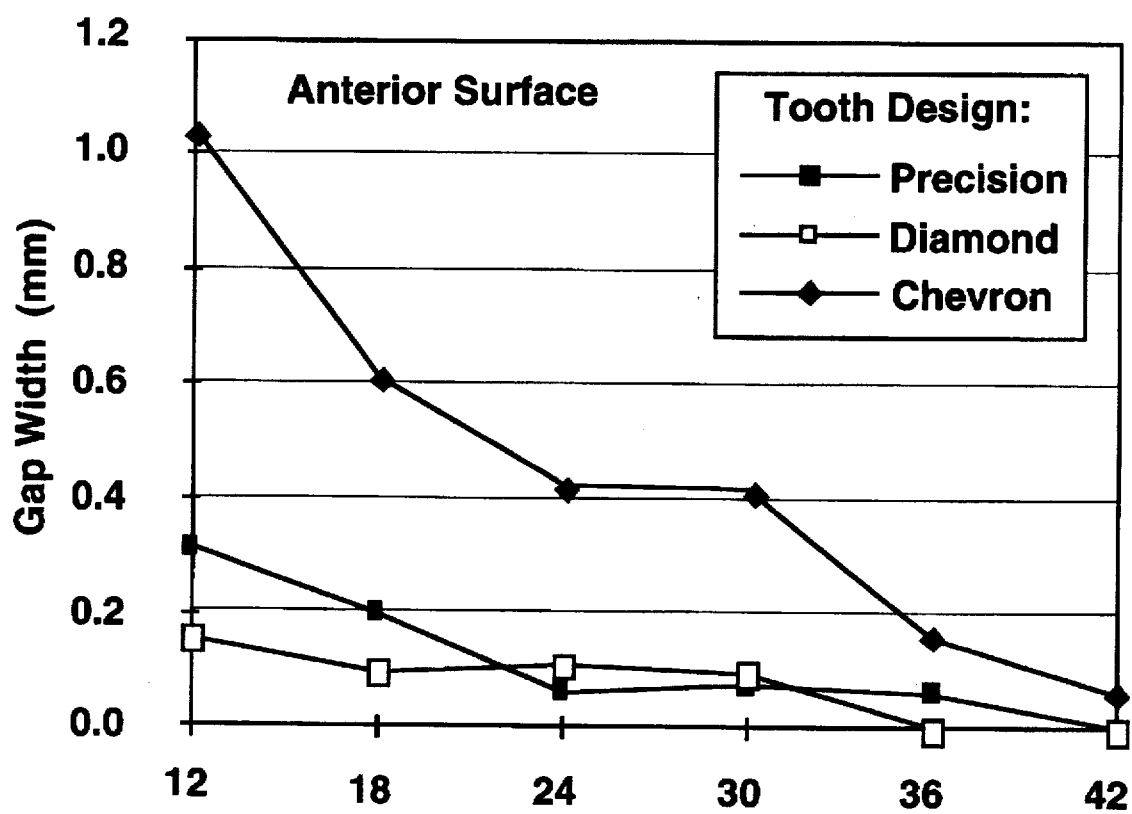
Figure 10. Distribution of Broach-Bone gaps along the anterior surface of the broach.

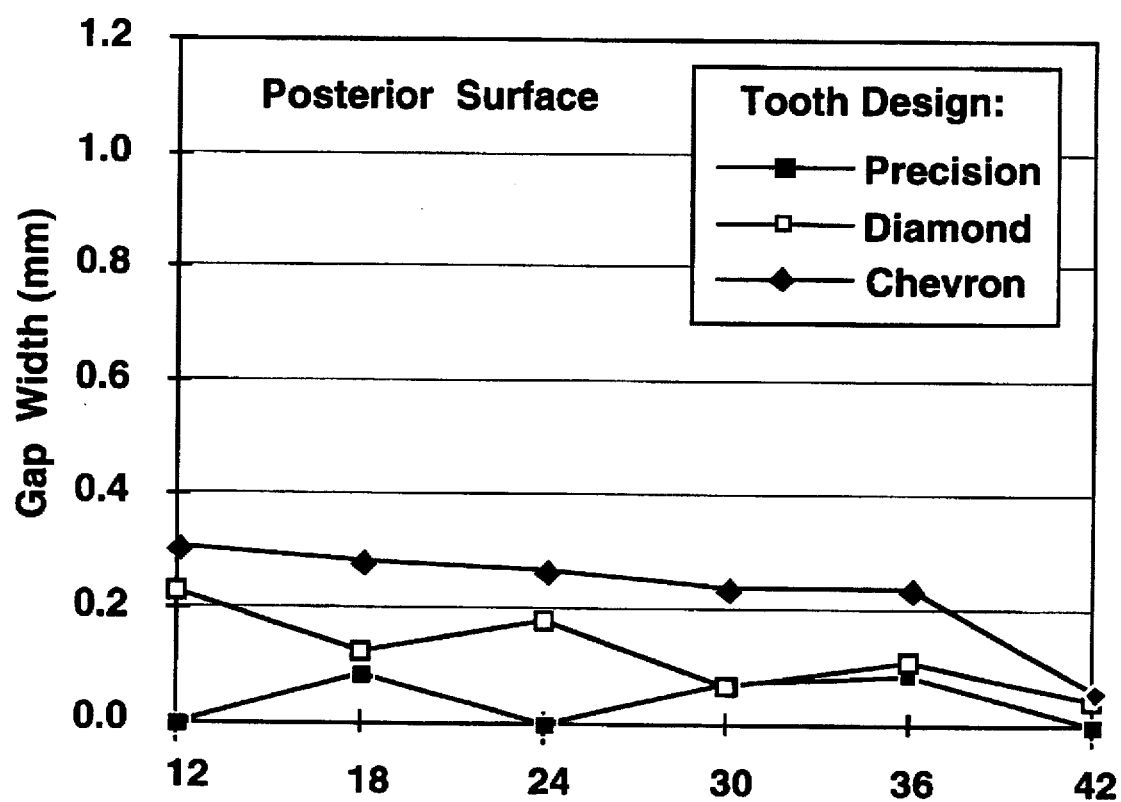
Figure 11. Distribution of Broach-Bone gaps along the posterior surface of the broach.

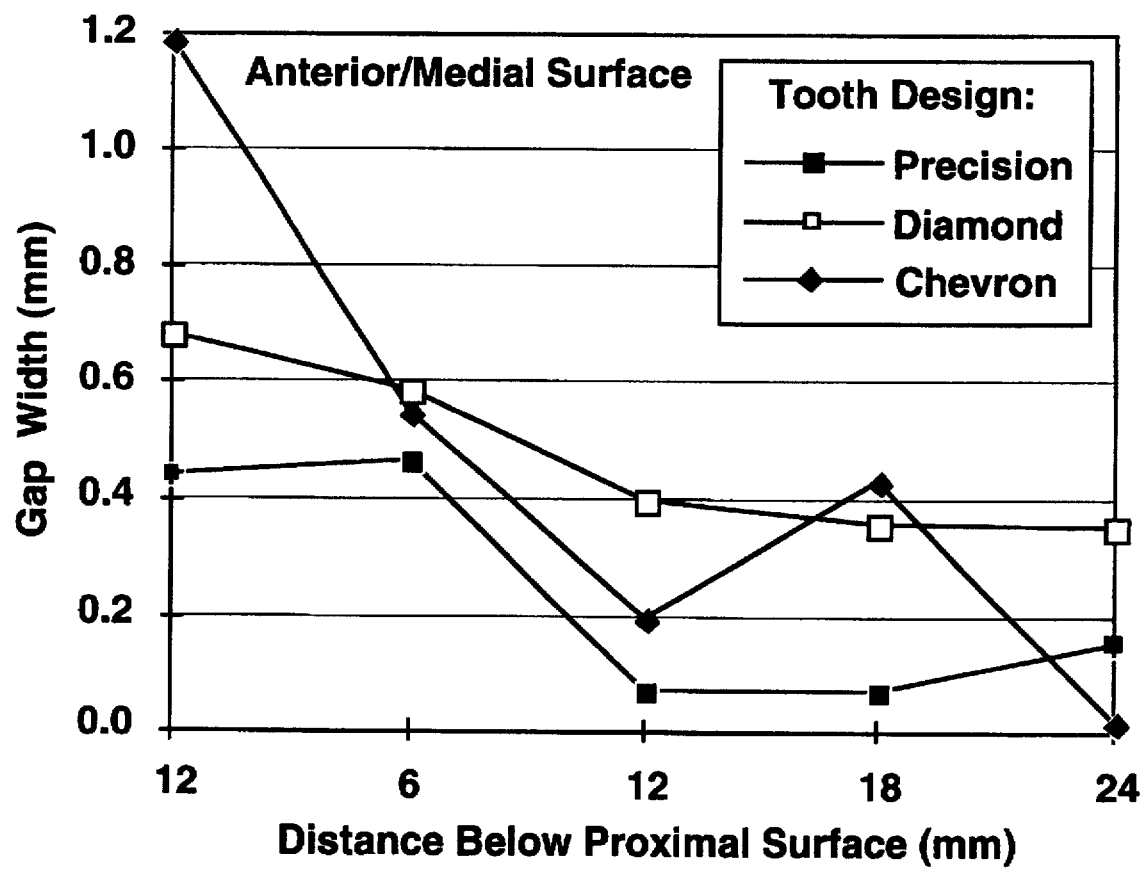
Figure 12. Distribution of Broach-Bone gaps along the anterior/medial surface of the broach.

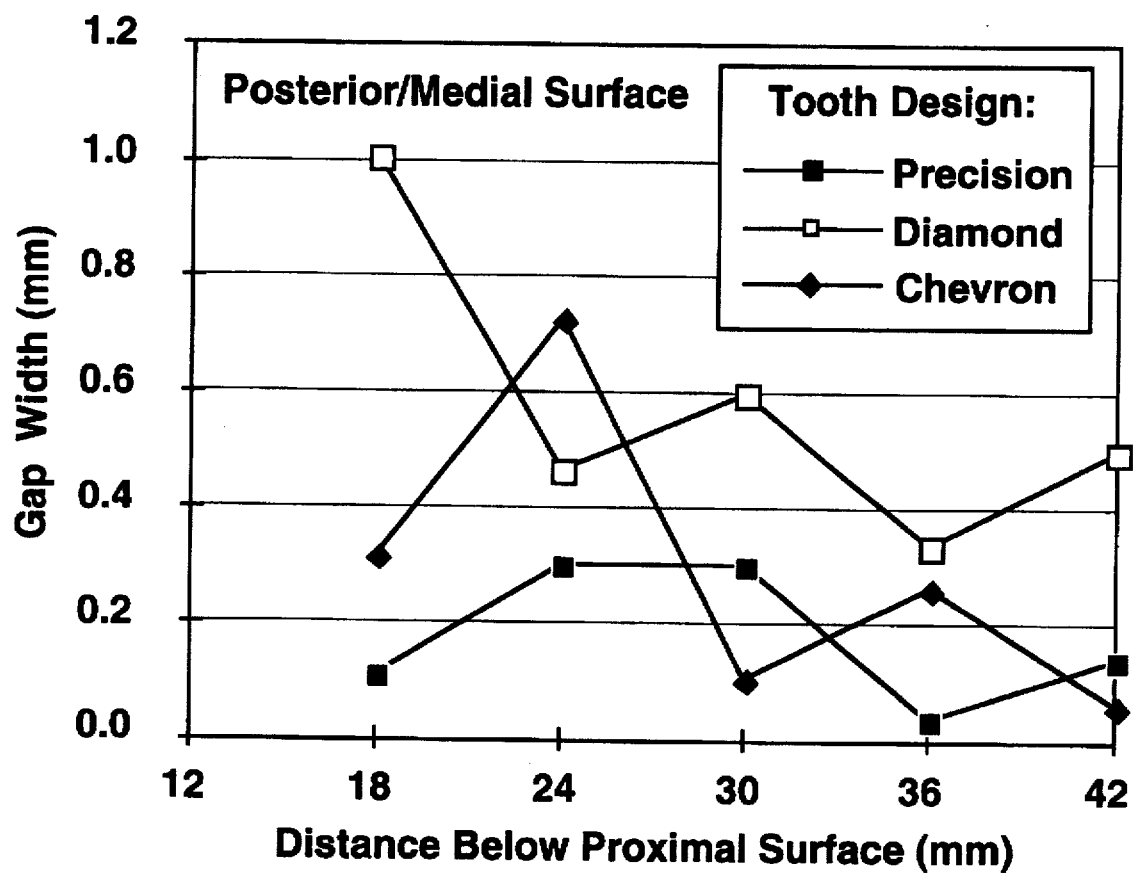
Figure 13. Distribution of Broach-Bone gaps along the posterior/medial surface of the broach.

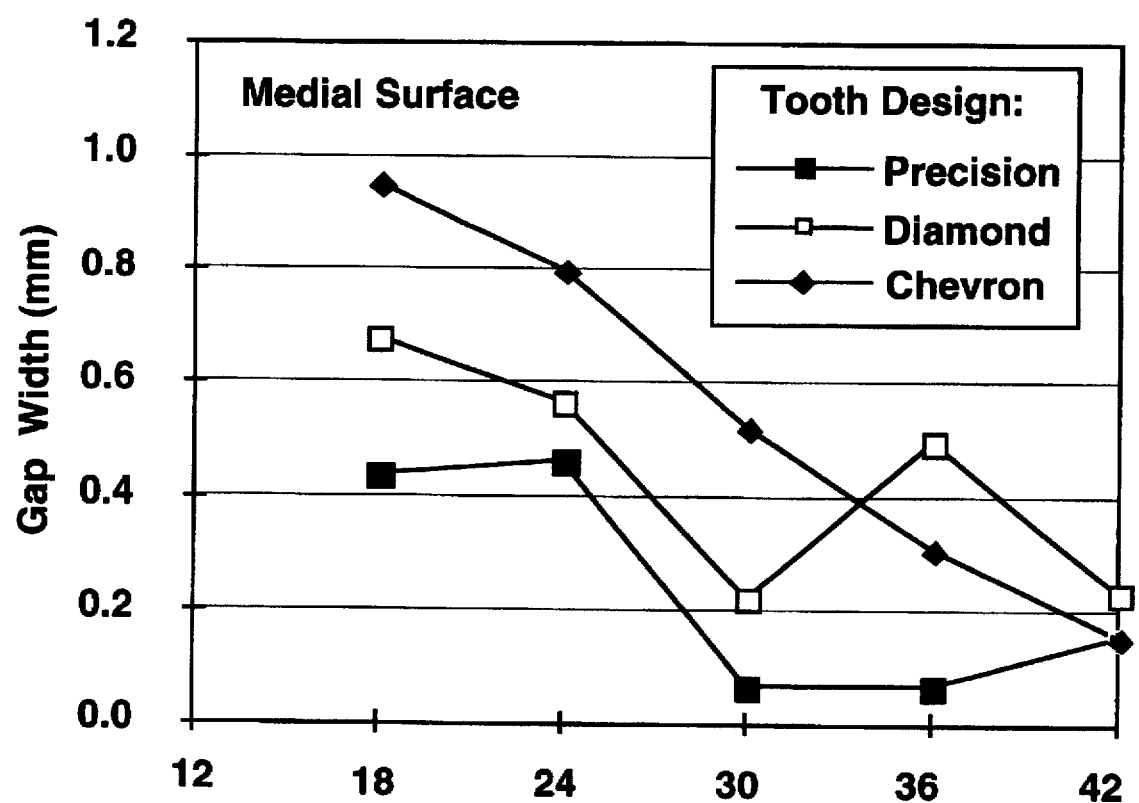
Figure 14. Distribution of Broach-Bone gaps along the medial surface of the broach.

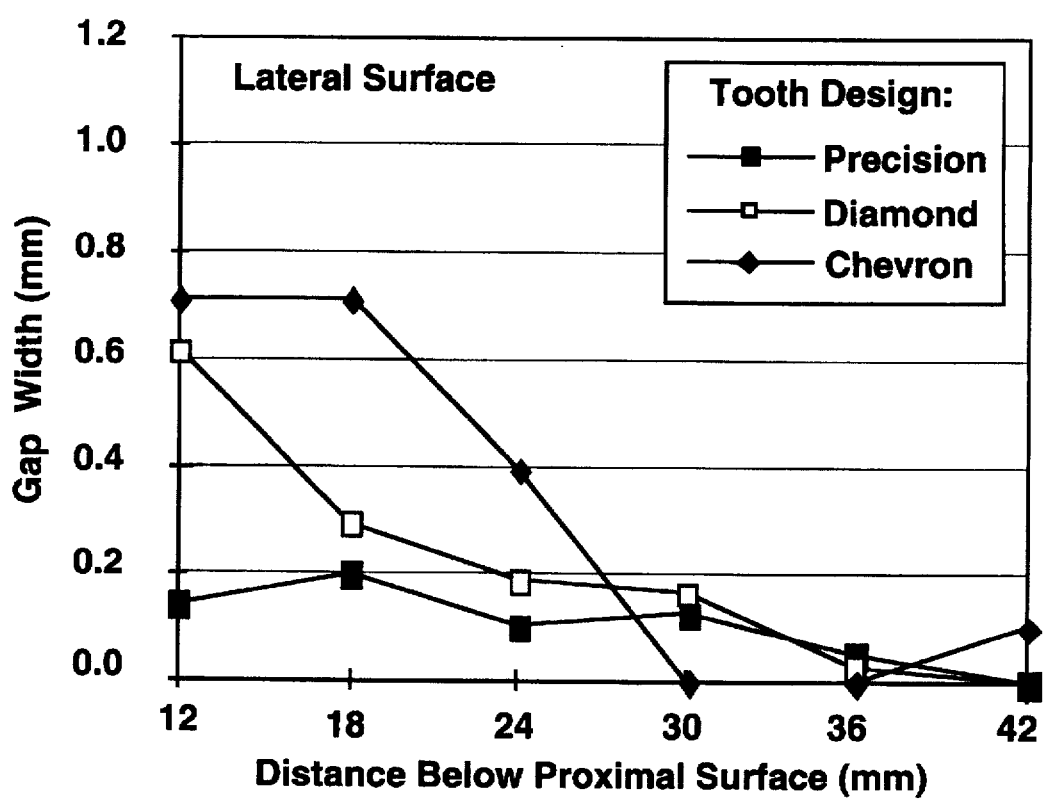
Figure 15. Distribution of Broach-Bone gaps along the lateral surface of the broach.

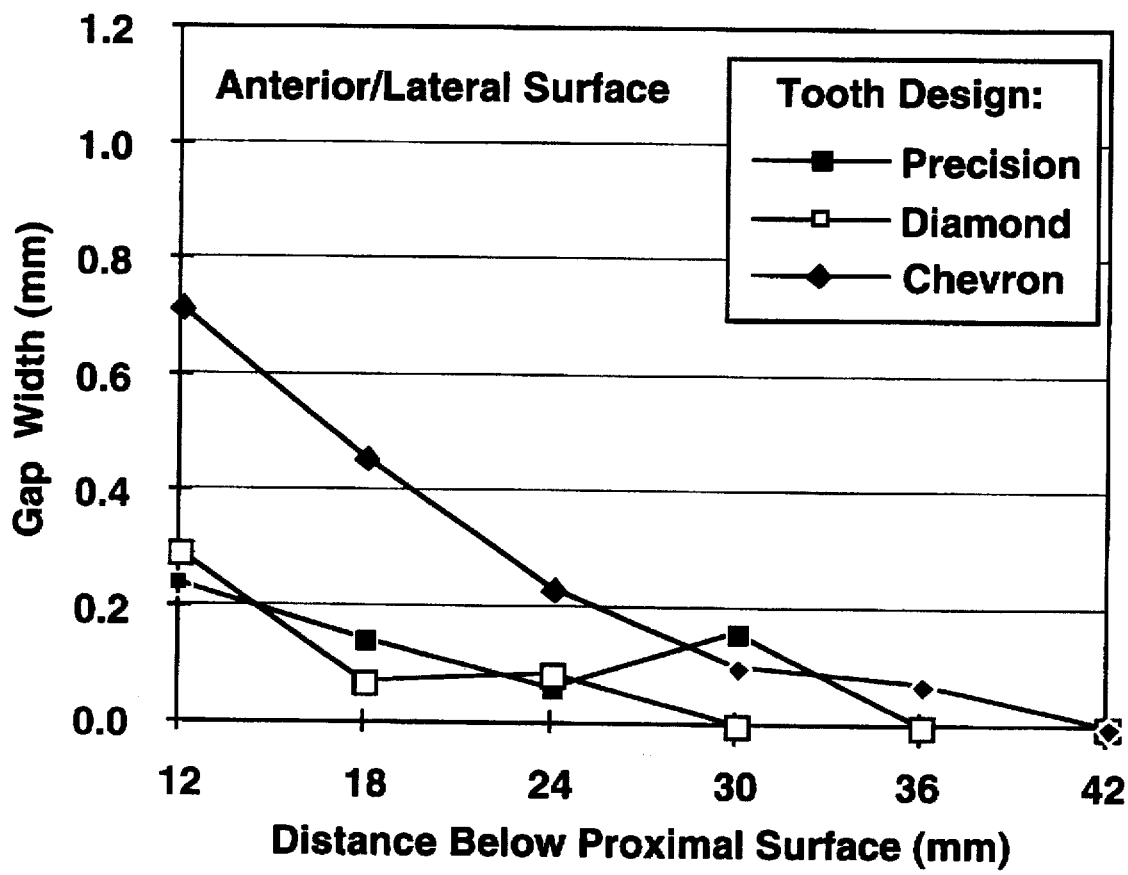
Figure 16. Distribution of Broach-Bone gaps along the anterior/lateral surface of the broach.

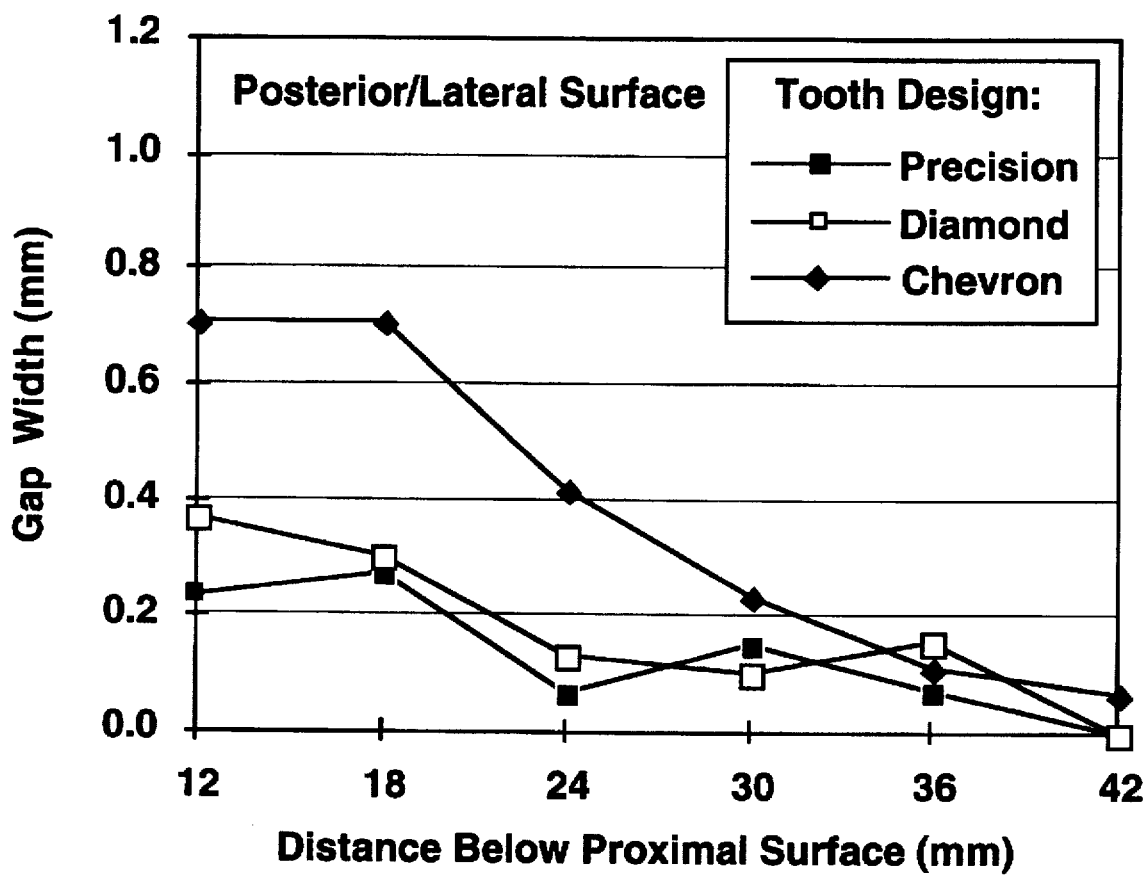
Figure 17. Distribution of Broach-Bone gaps along the posterior/lateral surface of the broach.

SURGICAL BROACH

BACKGROUND OF INVENTION

1. Field of Invention

The present invention is directed to a broach for preparing an intramedullary canal of a bone for receiving the stem component of a prosthesis. Specifically, the present invention is directed to an improved broach designed for optimizing the balance between surgical ease-of-use and minimal gap formation between the prosthesis and the intramedullary canal.

2. Background of Invention

The preparation of the intramedullary canal for receiving a femoral prosthesis is a critical step in cementless hip arthroplasty procedures since the fit between the stem and its associated femur is determined by the size of the prepared cavity. An improper fit of the stem within the cavity often causes microrotation of the stem relative to the femur and unstable fixation.

A major source of early loosening and failure of the prosthesis is misalignment of the prosthesis so that its proximal end is inclined medially with respect to the longitudinal axis of the medullary canal. This misalignment occurs because the broach is implanted in varus, and thus produces a cavity that is not correctly aligned. Implantation of the broach in the neutral position minimizes the possibly of misalignment; however, such implantation requires that the lateral face of the broach cut into the very hard bone of the greater trochanter, which is difficult to penetrate with conventional broaching instruments. Specifically, in the posterior-lateral corner of the implantation site hard bone is often present due to a condensation of cancellous bone which must be machined away to allow the broach to be neutrally aligned. Conventional broach teeth are normally not sufficiently aggressive to remove this bone. In addition, the trochanter is covered with tough tissue which clogs the teeth of the cutting instruments, thus rendering them ineffective in cutting bone.

It has therefore been recognized in the art that in order to remove the strong trochanteric bone, the lateral surface of the broaching instrument must have aggressively cutting teeth. Historically, femora were prepared with bone rasps covered with diamond or hook-shaped teeth. Such bone rasps were relatively easy to use and fairly effective in removing bone, especially if their surface features were coarse. However, such rasps made ragged cavities and were not suitable for applications in which a precise implant/bone fit was important. Moreover, increasing evidence suggests that the presence of gaps at the cementless interface facilitates osteolysis. Consequently, it is essential that the cavity formed within the femur by broaching closely replicates the dimensions of the instrument itself.

In practice, hand broaching is a relatively inaccurate method of machining the proximal femur due to three main factors:

(1) The instrument is not precisely directed. Deviations in the "tool path" of the instrument are reflected in an enlarged cutting envelope leading to gaps at the stem/ bone interface. This effect is especially pronounced with aggressive tooth configurations which allow the broach to machine bone wherever the instrument is directed.

(2) The cutting surface erodes bone and does not cut it cleanly. Upon insertion and subsequent extraction, the broach breaks trabeculae and drags them along the interface. This causes a ragged surface which is further enlarged beyond the broach envelope.

(3) The broach acts as a wedge and causes the femur to expand elastically. Upon removal, the implantation site contracts and so may be smaller than the broach if a significant amount of cancellous bone was removed when the bone was in an expanded state.

The foregoing problems are of particular concern when broaching the medial, anterior/medial, and posterior/medial surfaces of the femoral canal, since these are crucial areas for attachment of the femoral stem within the femur. Thus, it is important that these areas be cut accurately and cleanly with very minimal gap formation resulting between the implant and the intramedullary canal.

While there exist several types of broaches, it is believed that none of them teach or suggest the strategic placement of a plurality of teeth having at least two different tooth configurations on a broach to optimize broaching efficiency while at the same time minimizing subsequent gap formation. The vast majority of such broaches comprise a single tooth configuration positioned about the entire surface of the broach, such as those disclosed in U.S. Pat. No. 4,552,136 (Kenna) and U.S. Pat. No. 5,041,118 (Wasilewski), for example. In Kenna, the teeth comprise a single cutting edge and are positioned about the entire surface of the broach with the exception of the distal lateral face and the proximal medial face, which are left substantially blank to avoid gouging of the lateral cortex and medial cortex, respectively. Wasilewski discloses a broach comprising cutting teeth having the same configuration with two pairs of cutting edges, wherein the cutting teeth are positioned on all four faces of the broach. U.S. Pat. No. 5,454,815 (Geisser et. al) is directed to a disposable broach designed for single use and comprises two types of cutting teeth: "course teeth" positioned in the distal, midshaft, and approximately lower third of the proximal regions and "fine" teeth positioned adjacent the course teeth in the proximal region. While Geisser et al. contends that the teeth allow for a "swift and at the same time gentle working of the bone" (col. 2, lines 66–67), there is no teaching as to the strategic placement of teeth to provide for optimal ease of use and cutting efficiency while effecting minimal gap formation, since each of the types of teeth disclosed are positioned on each face of the broach.

Consequently, it is desireable to have a broach that allows for fast and efficient removal of bone, including hard bone that is difficult to remove, while simultaneously minimizing gap formation between the prosthesis and the intramedullary canal, thereby minimizing early loosening and failure of the implant, in particular in procedures wherein a precise implant/bone fit is important.

SUMMARY OF THE INVENTION

The present invention is directed to an improved broach for preparing an intramedullary canal of a bone. More particularly, the inventive broach comprises a plurality of cutting teeth having at least two different configurations which are positioned on different areas of the cutting surface of the broach for optimal cutting efficiency, surgical ease-of-use, and minimal gap formation between the prosthesis and the intramedullary canal.

Preferred embodiments of the inventive broach comprise (a) a longitudinal axis; (b) anterior, posterior, lateral, and medial faces; and (c) a plurality of cutting teeth having different tooth configurations, including a first set of teeth positioned on the lateral face and a second set of teeth positioned on at least one of the anterior and posterior faces, wherein each tooth of the first set of teeth has a different configuration from each of the second set of teeth. Most preferably, the lateral face comprises cutting teeth having multiple cutting edges designed for aggressive bone cutting, particularly within areas of the intramedullary canal containing strong bone that is difficult to remove.

In the most preferred embodiment, the broach further includes at least three different tooth configurations positioned on one or more of the broach faces, most preferably all four faces of the broach. The design and positioning of these different types of cutting teeth improve the overall machining efficiency and speed of the broach, but minimize gap formation between the prosthesis and the implant, especially in the crucial areas of the intramedullary canal where gaps between the prosthesis and the inner bone surface tend to cause the most serious problems clinically.

The first preferred tooth configuration of the present invention comprises a cutting tooth having a trailing face, a leading face, and a flat portion therebetween, with the flat portion further including a single cutting edge. Most preferably the tooth has a rake angle of about 0 degrees and a relief angle of about 25 degrees (referred in Examples 1 and 2 as the "Standard design"). The Standard design is particularly conducive in effecting minimal gap formation, and thus is preferably positioned on the medial face, anterior/medial corner, and posterior/medial corner of the broach.

The second preferred tooth configuration is a diamond-shaped tooth (i.e. "Diamond" tooth design) which has multiple cutting edges and is thus particularly effective for aggressive bone cutting. Most preferably, the Diamond tooth design has a relief angle of about 45 degrees and a rake angle of about −25 degrees.

The third preferred tooth configuration (referred in Examples 1 and 2 as the "Chevron" design, for reasons which will be discussed later) is similar to the Standard design in that it has a trailing face, a leading face, and a flat portion therebetween, wherein the flat portion further has a cutting edge. However, most preferably this third design also has two additional cutting edges, a relief angle of about 20 degrees, and a rake angle of about 0 degrees. In the most preferred embodiment, these teeth are employed on the anterior and posterior faces in parallel rows positioned at about 60 degrees to the cutting direction of the broach (i.e. the longitudinal axis). In combination with a plurality of concavities or "chip breakers" positioned between adjacent teeth within each row, these teeth are also conducive to fast and efficient bone cutting, thereby making the broach easier to use.

BRIEF DESCRIPTION OF THE DRAWINGS

FIGS. 10–17 are graphs illustrating the distribution of broach-bone gaps along various surfaces of different broaches. The data shown in each graph was derived from an experimental study described in Example 1.

DETAILED DESCRIPTION OF THE PREFERRED EMBODIMENTS

The present invention is directed to an improved broach comprising a plurality of teeth designed to prepare an intramedullary canal of a mammalian bone. The inventive broach may be used to prepare any mammalian bone, including but not limited to the long bones of the body such as the humerus, tibia, distal femur, and proximal femur, for implantation of a prosthesis. However, for ease of explanation, the present invention will be described herein with reference to the preparation of the proximal femur for implantation of a femoral stem in cementless hip arthroplastic procedures. It is contemplated that one of ordinary skill in the art, having the benefit of the teachings and suggestions presented herein, will be capable of modifying the inventive broach as necessary to achieve the same results in other bones requiring the implantation of a prosthesis within an intramedullary canal.

It has been discovered that significant differences exist between the performance of broaches with cutting teeth of different geometric configurations with respect to the accuracy of cavities formed within the proximal femur (see Example 1). While certain cutting teeth allow the broach to cut bone efficiently, gap formation within the femoral canal tends to be a significant and serious concern in critical areas of prosthetic attachment within the femur, as discussed in Example 2. However, in order to remove effectively hard trochanteric bone for implantation of the femoral stem in a neutral position (thus minimizing early loosening and failure of the stem, as discussed earlier), the lateral face of the broach must include aggressive cutting teeth, such as diamond-shaped teeth or other types of rasp-like teeth having multiple cutting edges and relief and rake angles conducive to aggressive bone cutting. Conversely, it is not desireable to employ such teeth on other faces of the broach because of the susceptibility of gap formation between the prosthesis and bone canal.

As a result, the present invention, in certain embodiments, is directed to an improved femoral broach comprising a plurality of cutting teeth having different tooth configurations positioned on different areas of the cutting surface of the broach which, in combination, serve to improve the speed and efficiency of bone cutting as well as minimize gap formation between the prosthesis and the femoral canal.

Figure 1:
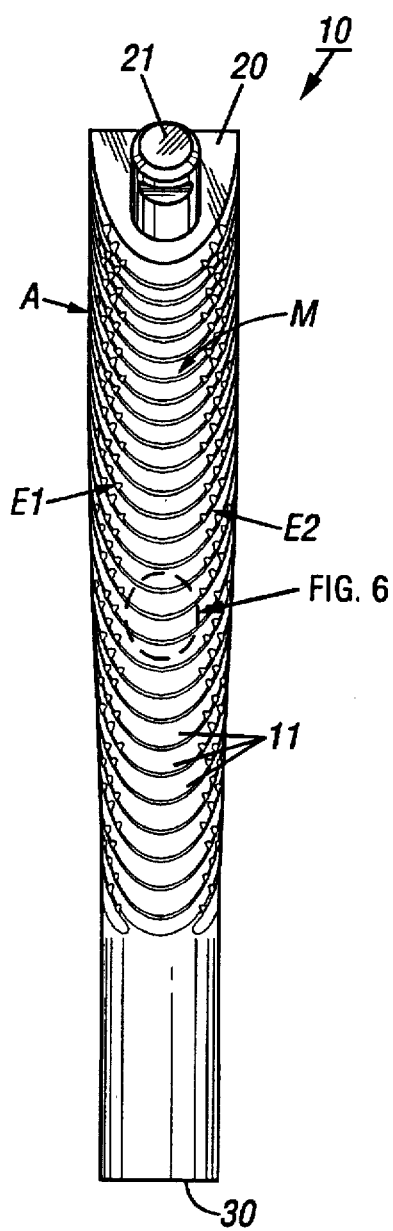
FIG. 1 is an elevated medial view of the broach.
Figure 2:
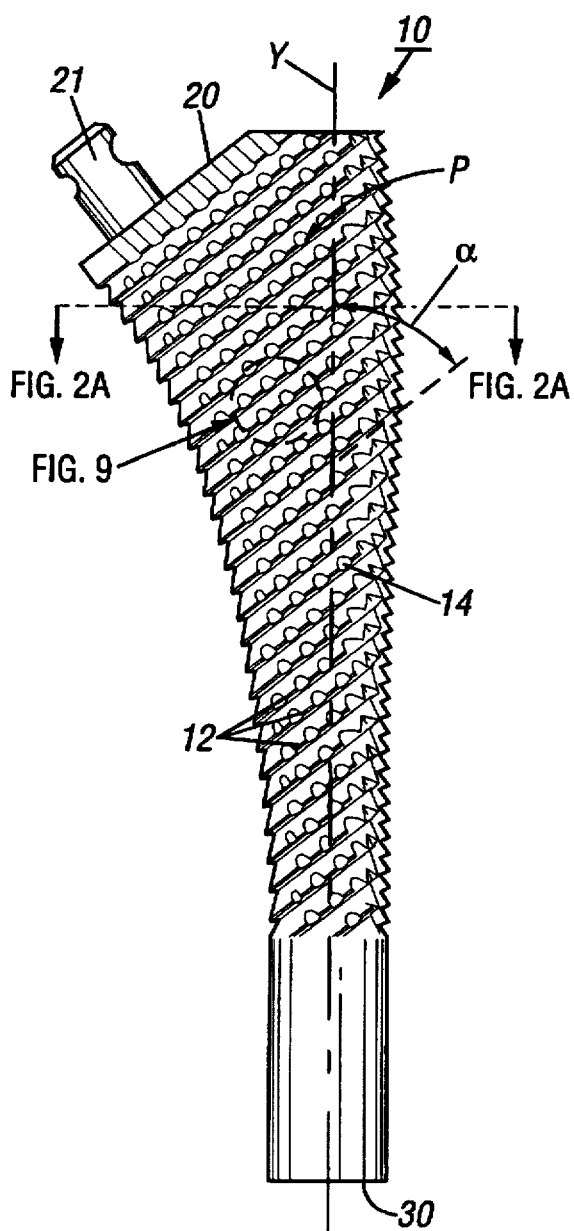
FIG. 2 is an elevated posterior view of the broach.
Figure 3:
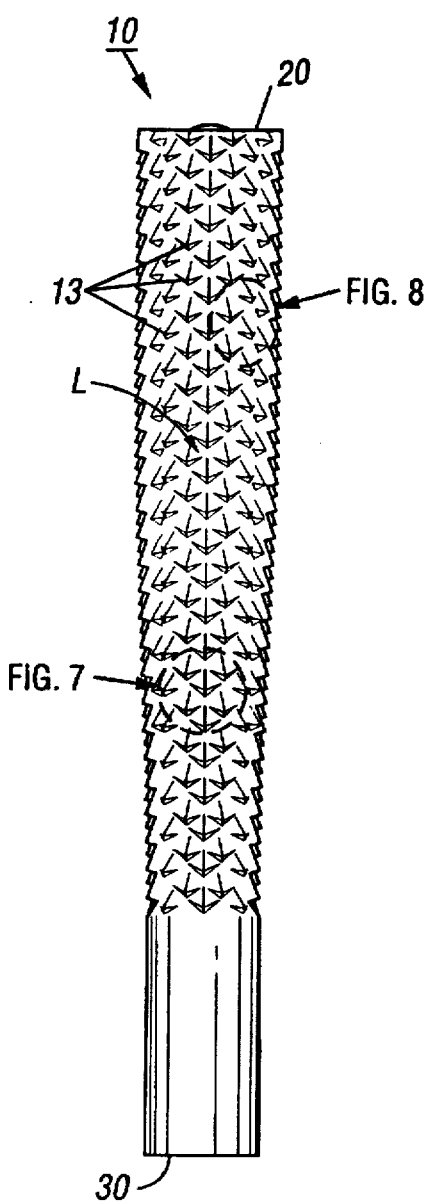
FIG. 3 is an elevated lateral view of the broach.

Similar to many conventional broaches, the inventive broach (10) comprises an anterior (A) face (partially shown in FIGS. 1 and 3), a posterior (P) face, a medial face (M), and a lateral (L) face, as well as anterior/medial (El) and posterior/medial (E2) corners as shown in FIGS. 1–3. Moreover, the broach is shaped very similarly to a femoral stem component, having a substantially flared proximal end (20) and a relatively narrow and substantially cylindrical distal end (30). The broach may be fabricated in different sizes to accommodate various femoral implant sizes and shapes, including but not limited to, asymmetric, symmetric, canted, and twisted stems. In addition, conventional materials may be used to manufacture the broach, including, but not limited to, various metal and metal alloys, such as stainless steels and cobalt-chromium (Co—Cr) alloys, as well as various hard polymeric materials. The most preferred material, however, is 17—4ph stainless steel.

Figure 4:
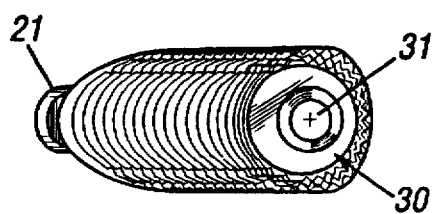
FIG. 4 is bottom plan view of the broach.

As illustrated in FIG. 4, the distal end (30) of the broach comprises a threaded socket (31) aligned parallel with the femoral axis (Y) of the broach for engaging a modular tip (not shown) designed to fit securely within the femoral cavity to keep the broach in alignment during the cutting process. As illustrated in FIG. 5, the proximal end (20) of the broach is similar to that of many conventional broaches and comprises a combination trunion (21), groove (22), and threaded hole (23) for engaging an inserter (not shown).

Figure 2A:
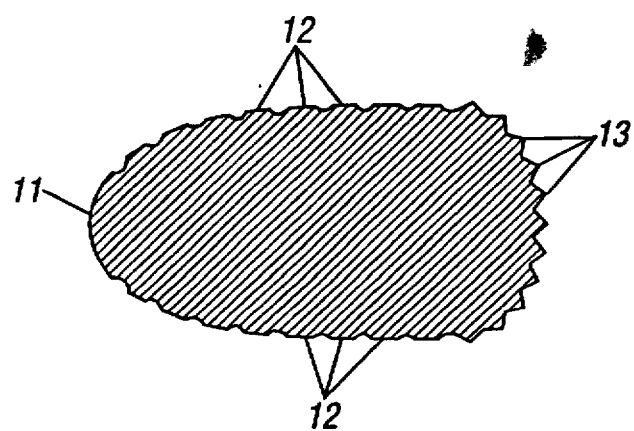
FIG. 2A is a cross-sectional view taken along lines 2A—2A of FIG. 2.

Sections I and II below discuss in detail the three preferred tooth configurations and their optimal positioning on the broach, respectively. However, it is important to note that the present invention in its broadest sense is directed to a femoral broach comprising a plurality of cutting teeth having different configurations, including, but not limited to, the tooth configurations described herein, and wherein said cutting teeth are optimally placed on the broach to minimize gap formation while improving overall cutting efficiency and speed. Specifically, as illustrated in FIG. 2A, the plurality of teeth are positioned on the inventive broach such that a cross section taken perpendicular to the femoral axis (Y) comprises at least two different configurations. Thus, it is contemplated that one of ordinary skill in the art, having the benefit of this invention's suggestions and teachings contained herein, could modify the cutting teeth described herein and/or the positioning of said teeth on the broach without departing from the scope or spirit of the present invention. For ease of explanation, however, the present invention will be discussed with reference to the most preferred embodiments as illustrated in the figures.

I. Configurations of cutting teeth:

As illustrated in FIGS. 1–3, the most preferred embodiment of the inventive broach comprises three different tooth configurations. In manufacturing the broach, a three-dimensional model is first constructed using standard modeling techniques and UNIGRAPHICS software (vended by EDS). The resulting 3-D model and ICAD software is utilized in the creation of tool cutter path geometry for the actual fabrication of the broach tool by a 6-axis CNC grinder.

The foregoing method of manufacture allows for the commercial fabrication of the present invention. It should be noted, however, that the most preferred or "ideal" rake and relief angles of the individual cutting teeth can be better achieved by hand-grinding the broach, as opposed to using machining methods. Nevertheless, the advantages of using machined fabrication methods, most preferably the method described above utilizing a 6-axis CNC grinder, far outweigh hand-grinding in terms of speed and ease of manufacture, accuracy, and reproducibility. Moreover, the foregoing machining method still provides a broach that achieves the objects of the present invention, namely a broach comprising optimally placed cutting teeth of different configurations, each tooth having rake and relief angles well within the preferred angle ranges, in particular the more functionally important rake angles, thus allowing for improved cutting efficiency and speed with minimal gap formation between the prosthesis and the intramedullary canal.

Figure 6:
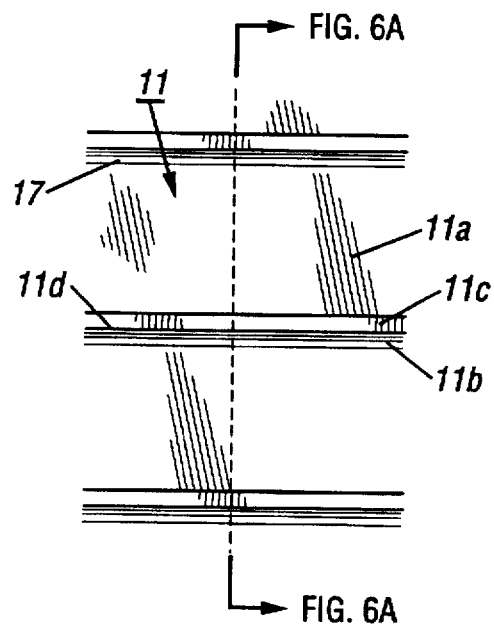
FIG. 6 is an enlarged view of the first tooth configuration as shown in FIG. 1.
Figure 6A:
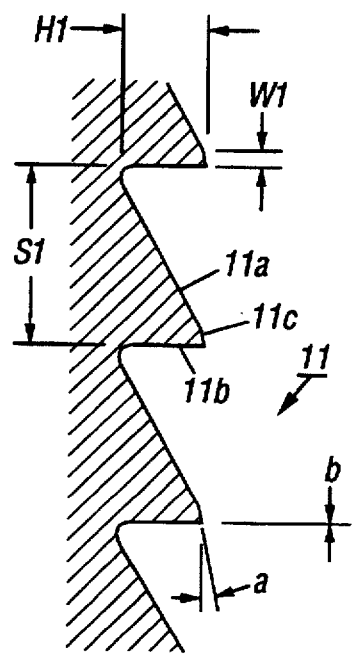
FIG. 6A is a cross-sectional side view taken along lines 6A—6A of FIG. 6.

The first cutting tooth design (11) is illustrated in FIGS. 1, 6, and 6A and referred in the studies described in Examples 1 and 2 as the "Standard" design tooth. The Standard tooth (11) is generally less aggressive in removing bone that other configurations of cutting teeth commonly used in bone rasps and broaches. The Standard tooth design comprises a substantially horizontal leading face (11b) and a trailing face (11a) angled relative to the longitudinal axis (Y) of the broach wherein the two faces converge to form a flat portion (11c) therebetween, resulting in a relief angle (a) of from about 0 degrees to about 60 degrees, most preferably about 25 degrees, relative to the longitudinal axis (Y), and a rake angle (b) of from about −10 degrees to about 10 degrees, most preferably about 0 degrees, relative to the longitudinal axis (Y). The Standard tooth design further includes a single cutting edge (11d) extending from the flat portion (11c) and cuts only on the downward stroke of the broach.

The preferred tooth height (H1) is from about 0.05 to about 0.07 inches. For smaller broaches, the preferred height is about 0.05 inches. The preferred width (W1) of the flat portion (11c) is from about 0.005 to about 0.020 inches, most preferably about 0.015 inches. The preferred tooth spacing (S1) is from about 0.13 to about 0.16 inches; however, for smaller broaches, the preferred spacing is more preferably about 0.13 inches.

The Standard tooth (11) is an improved variation of the tooth design of the broach of the PRECISION HIP SYSTEM, vended by Howmedica, Inc. In broaches of this design, the cutting teeth have a relief angle of 15 degrees. This modification in relief angle results in an improved cutting tooth that is believed to be more durable than, and has been found to remove bone at three to five times the rate of, the PRECISION HIP broaches.

Figure 7A:
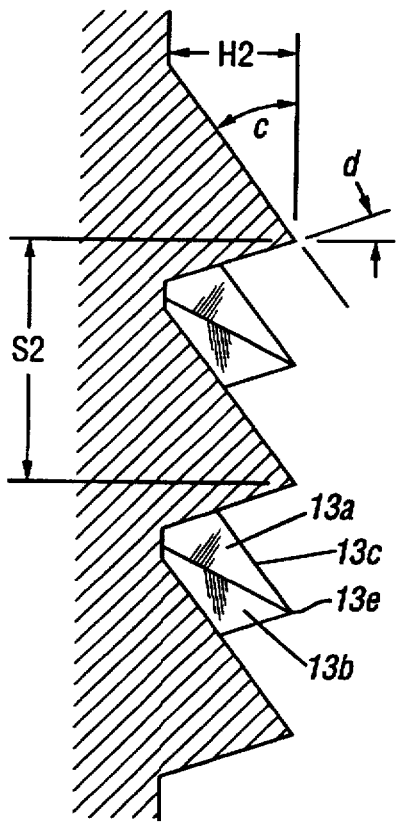
FIG. 7A is a cross-sectional side view taken along lines 7A—7A of FIG. 7.
Figure 7:
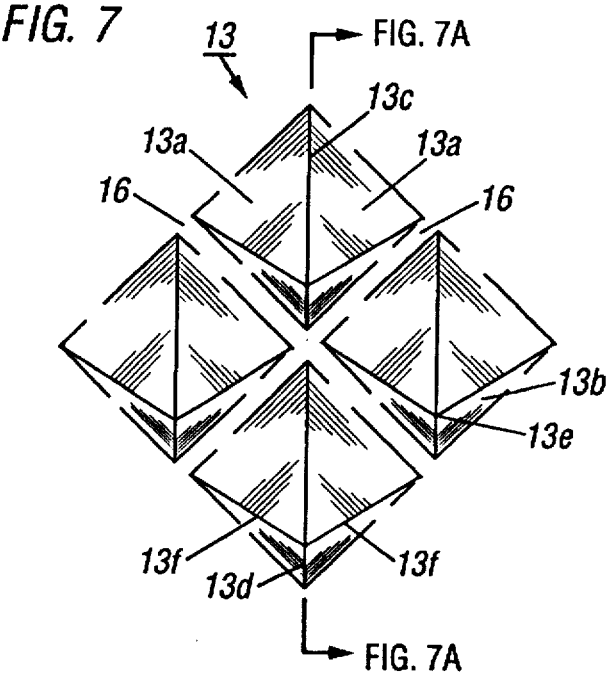
FIG. 7 is an enlarged view of the second tooth configuration shown in FIG. 3.
Figure 8:
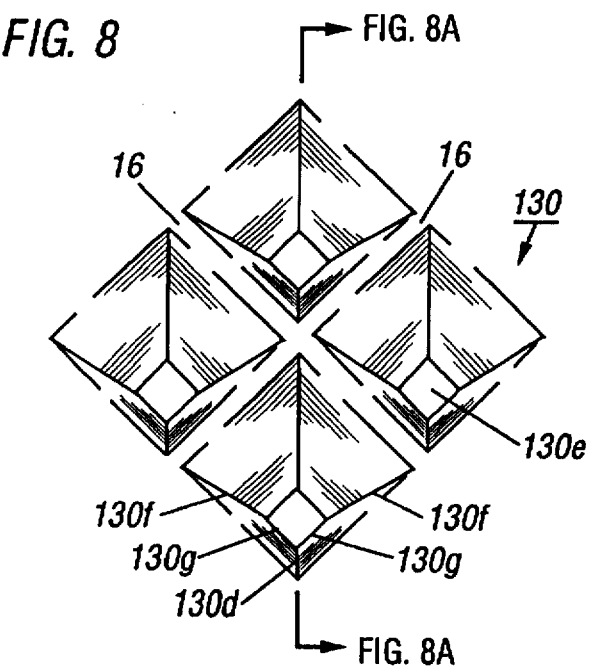
FIG. 8 is an enlarged view of a fourth tooth configuration as shown in FIG. 3.
Figure 8A:
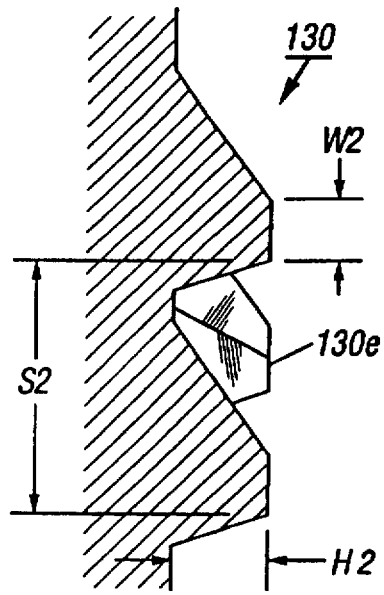
FIG. 8A is a cross-sectional side view taken along lines 8A—8A of FIG. 8.

The second cutting tooth design (13) is substantially diamond shaped (referred herein as the "Diamond" tooth design) and is illustrated in FIGS. 3, 7, and 7A. Each Diamond tooth (13) comprises two adjacent leading faces (13b) converging to form a leading cutting edge (13d) and two adjacent trailing faces (13a) converging to form a trailing edge (13c). When viewed from the side, as shown in FIG. 7A, for example, the Diamond tooth has the appearance of a "slanted pyramid", wherein the relief angle (c) is from about 20 degrees to about 60 degrees relative to the longitudinal axis (Y), most preferably about 45 degrees, and the rake angle (d) is from about −10 degrees to −40 degrees, most preferably about −25 degrees, relative to the longitudinal axis (Y). In the preferred embodiment, the Diamond tooth may have a substantially pointed tip (13e) as shown in FIGS. 7 and 7A, for example, or it may comprise a flat portion (130e), as shown in FIGS. 8 and 8A. The Diamond teeth also have multiple cutting edges which allow for aggressive bone cutting. In the first embodiment having a substantially pointed tip (FIGS. 7 and 7A), the tooth has cutting edge (13f) formed at the junction between the leading and trailing faces and cutting edge (13d) formed at the junction between the two leading faces. The second embodiment of the Diamond tooth having a flat portion (FIGS. 8 and 8A) has similar cutting edges (130f and 130d) and further includes cutting edges (130g) formed by the flat portion (130e). In this latter embodiment, the preferred width (W2) of the flat portion is from about 0.005 to about 0.020 inches, most preferably about 0.015 inches.

The preferred tooth height (H2) and tooth spacing (S2) for both embodiments of the Diamond tooth is the same as for the Standard tooth.

As discussed in Example 1, the Diamond teeth are capable of removing bone at over three times the rate of the Standard teeth and tend to accumulate less bone debris than the Standard tooth design. Consequently, teeth of this design should be included in areas where the most aggressive cutting action is required. This is true over the lateral face (L) of the broach which must remove bone from the greater trochanter. However, as the Diamond teeth tend to cause the greatest gaps, their location must be restricted to areas of the broach where corresponding regions of the femoral canal are less susceptible to gap formation, as discussed in more detail in Section II.

Figure 9:
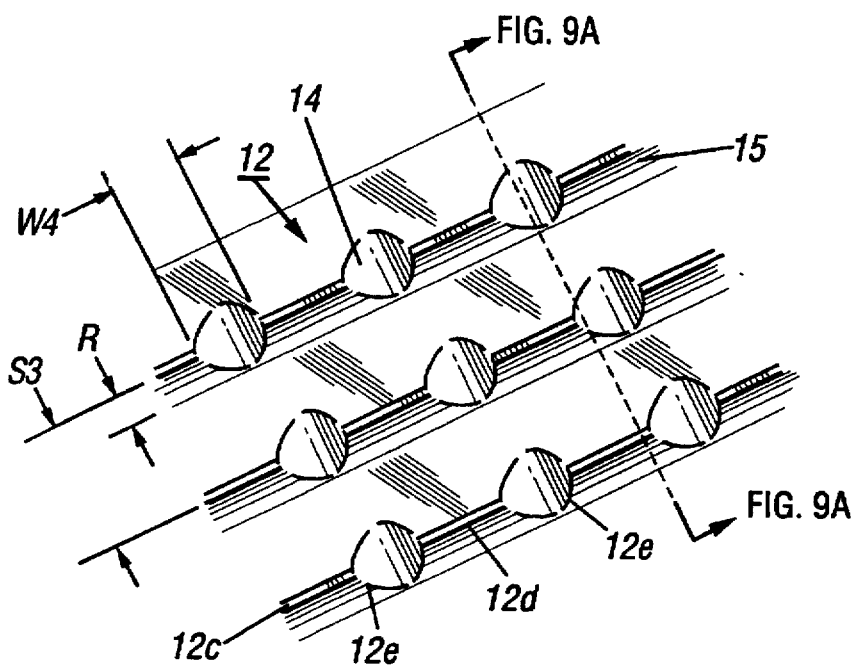
FIG. 9 is an enlarged view of the third tooth configuration shown in FIG. 2.
Figure 9B:
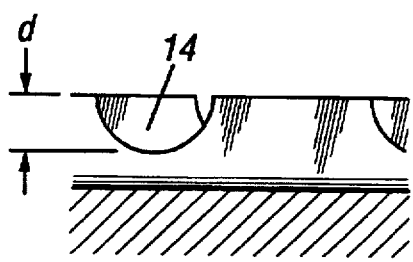
FIG. 9B is a sectional view taken along lines 9B—9B of FIG. 9A.
Figure 9A:
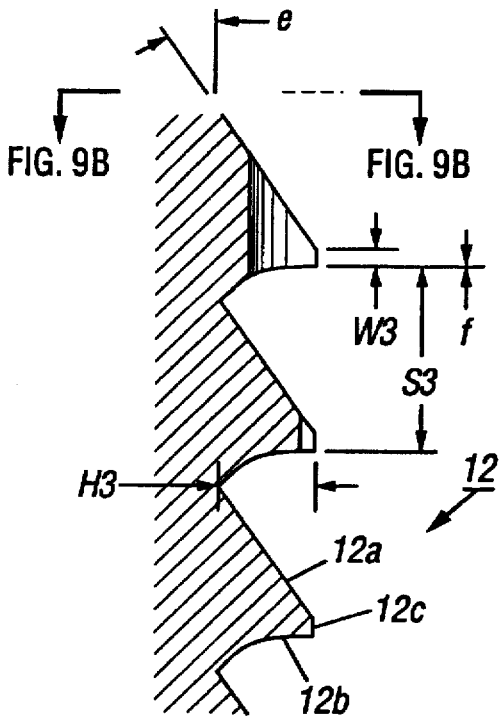
FIG. 9A is a cross-sectional side view taken along lines 9A—9A of FIG. 9A.

The third preferred tooth configuration (12) is illustrated in FIGS. 2, 9, and 9A and comprises a leading face (12b) and a trailing face (12a) which converge to form a flat portion (12c) therebetween. [This third tooth design is referred in Examples 1 and 2 as the "Chevron" design since in one type of broach tested these teeth were positioned in parallel rows that extended all around the broach surface from the anterior side to the lateral side and from the posterior side to the lateral side, thereby meeting along the lateral side of the broach to form a "V" configuration or "chevron" appearance. For purposes of clarity, the third tooth configuration will be referred herein as the "Chevron" tooth design.] Preferably, the Chevron tooth design (12) has a relief angle (e) of from about 15 degrees to 60 degrees and a rake angle (f) of from about from about −10 degrees to about 10 degrees. Most preferably, the relief angle (e) is about 20 degrees and the rake angle (f) is about 0 degrees, as shown in FIG. 9A. As shown in FIG. 2, the Chevron teeth (12) are preferably positioned on the posterior (P) and anterior (A) faces of the broach at a diagonal angle ($\alpha$) to the cutting direction (i.e. longitudinal axis (Y)) of the broach. Like the Standard tooth design (11), the Chevron teeth cut only on the downward stroke of the broach.

In the most preferred embodiment, the Chevron teeth are arranged in parallel rows (R), as shown in FIG. 2, at an angle ($\alpha$) ranging from about 40 degrees to about 85 degrees, most preferably 60 degrees, relative to the longitudinal axis (Y) of the broach. Cut within each row (R) between adjacent teeth is preferably a concavity (14) or "chip breaker" which aids in the removal of bone chips and other debris upon broaching. In addition, the Chevron tooth preferably includes multiple cutting edges, specifically cutting edge (12d) which is integral with flat portion (12c) and cutting edges (12e) which are integral with the concavity (14) and tangent to cutting edge (12d). Like the Diamond tooth described above, the Chevron tooth (12) is also capable of removing bone at over three times the rate of the Standard tooth design and also tends to accumulate less bone debris than the Standard design. However, like the Diamond design, the Chevron tooth tends to cause significant gaps (i.e. over 0.50 mm) in certain areas of the intramedullary canal.

The preferred tooth height (H3) and tooth spacing (S3) for the Chevron tooth is the same as that for the Diamond and Standard teeth discussed above. Similarly, the preferred width (W3) of the flat portion (12c) is from about 0.005 to about 0.020 inches, most preferably about 0.015 inches. The width (W4) of the concavity is preferably from about 0.08 to about 0.09 inches (most preferably 0.08 inches for smaller broaches). The preferred depth (d) of the concavity is from about 0.025 to about 0.04 inches (most preferably about 0.025 inches for smaller broaches).

II. Positioning of cutting teeth:

It has been discovered that in order to minimize gap formation in those areas of the femoral cavity most susceptible to gap formation, while at the same time maximizing ease-of-use and cutting efficiency, the cutting teeth are most preferably positioned on the broach as shown in FIGS. 1–3. For example, anatomical studies of the femoral canal upon broaching suggest that minimal gap formation occurs even after aggressive cutting within the lateral area of the canal (see Example 1). Further, in order to implant the stem in a neutral position, thereby minimizing the potential for early loosening and failure, it is necessary to remove strong trochanteric bone present laterally within the canal, as discussed above. Consequently, it is necessary to employ sharp cutting teeth effective in aggressively cutting strong bone in this region. Such teeth include multiple cutting edges and a means for allowing bone chips to be removed, such as chip breakers or channels, or example. Preferably, the "Diamond" cutting teeth are employed in the present invention and are positioned on the lateral (n) face of the broach. The Diamond teeth (13) are preferably arranged in a non-tracking formation, with a preferred spacing between each tooth of from about 0.13 to about 0.16 inches, as discussed above. As will be discussed in more detail below, the spacing between the Diamond teeth act as channels (16) to aid in the removal of bone chips and debris upon broaching. Alternatively, the broach may comprise a combination of Diamond teeth having substantially flattened tops (13θe) and sharp tops (13e) positioned on the lateral face (L), as shown in FIGS. 3, 7, and 8, as discussed above. The "flat" Diamond teeth (13θ) may be strategically placed on those portion(s) of the broach where there may be a greater than usual tendency for gap formation and/or where less aggressive bone cutting is required, most preferably in the proximal and mid sections of the broach (i.e. upper two-thirds), as shown in FIG. 3. Other types of sharp cutting teeth may also be employed on the lateral face, such as the Chevron tooth design (12) discussed herein, most preferably one having a rake angle of from about 0 degrees to 20 degrees, most preferably 20 degrees.

Conversely, it is very important that gap formation be minimized when broaching the medial, anterior/medial, and posterior/medial surfaces of the femoral canal, since these are crucial areas for support of the femoral stem within the femur to minimize implant/bone motion. Thus, it is very important that these areas be cut accurately and cleanly with very minimal gap formation. Consequently, the corresponding medial face (M) (and anterior/medial (E1) and posterior/medial corners (E2)) comprise less aggressively cutting teeth, most preferably the Standard tooth (11), as shown in FIG. 1. As discussed above, the Standard teeth (11) are preferably arranged in a single column on the medial face (M) and spaced from about 0.13 to about 0.16 inches apart, as discussed above. Alternatively, the medial face could comprise the teeth of the PRECISION HIP BROACH, as described above, in addition to, or in lieu of, the Standard teeth. Moreover, certain areas of the medial face (M) (or anterior/medial (E1) or posterior/medial corners (E2)) could remain blank, in particular those areas of the broach that come in contact with the corresponding areas of the femoral canal most critical for prosthetic attachment, for example.

As shown in FIG. 2, the Chevron teeth (12) are most preferably positioned on both the posterior (P) and anterior (A) faces of the broach, since the anterior and posterior sections of the proximal femur contain a large volume of relatively soft cancellous bone which does not need the aggressive cutting action of the Diamond teeth, for example.

To facilitate the removal of bone chips, the Chevron teeth are preferably arranged in parallel rows, wherein each row is further arranged at a diagonal angle ($\alpha$) relative to the longitudinal axis (Y) of the broach, as illustrated in FIGS. 2 and 9. This arrangement also enhances the cutting action of the broach because it allows the teeth to shear the material away as opposed to broaching. Because of the large volume of bone being removed in this area, a concavity (14) or "chip breaker" is positioned between adjacent Chevron teeth within each row (R). While not as efficient, the Chevron teeth may be positioned on the lateral face of the broach in addition to, or in lieu of, the Diamond teeth described above.

Figure 5A:
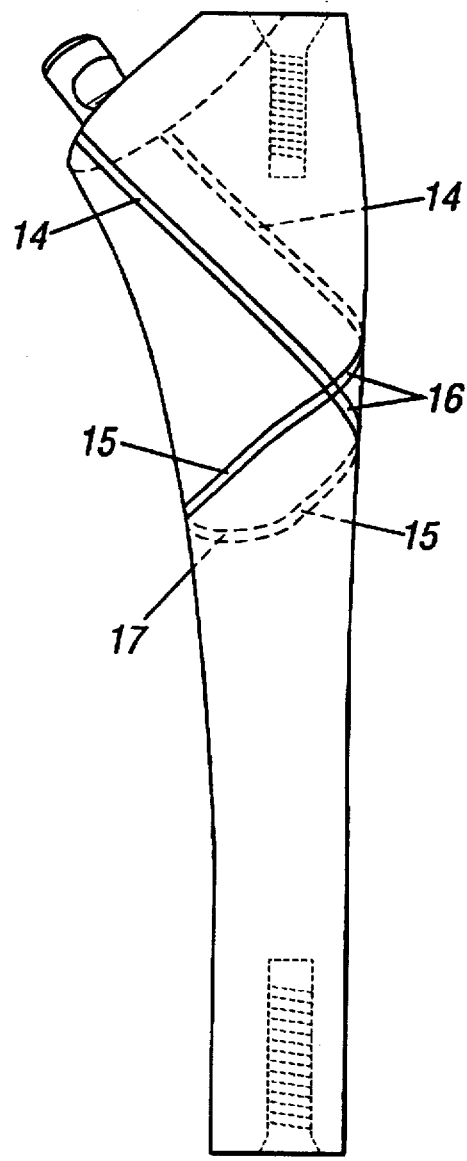
FIG. 5A is a front edge view of the posterior/lateral corner of the broach taken along lines 5A—5A of FIG. 5.
Figure 5:
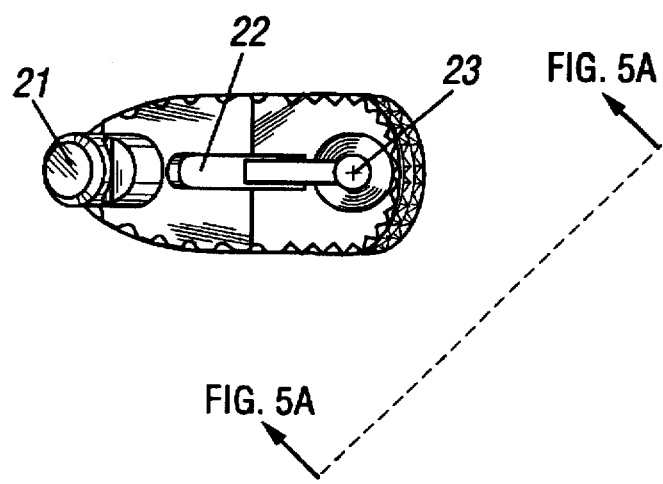
FIG. 5 is a top plan of the broach.

As shown in FIGS. 5A, 7, and 9, for example, the broach further includes channels (15) which are formed in part by the spacing between rows (R) of Chevron teeth on the anterior face (A) and posterior face (p) of the broach and extend to, and are integral with, the spacing (17) between the teeth (preferably the Standard or Precision teeth described herein) on the medial face (M). On the lateral face (L), the spacing between the Diamond teeth form channels (16) that extend distally toward and across the posterior and anterior faces and are integral with the channels (15) formed between the rows of Chevron teeth thereon. In the proximal direction, the channels (16) on the lateral face perpendicularly intersect the "row" channels (15) of the anterior and posterior faces at the anterior/lateral and posterior/lateral edges of the broach and are substantially in line with the concavities (14) present on the anterior and posterior faces. [FIG. 5A is a schematic posterior/lateral edge view illustrating the relative positioning and relationship among the posterior face concavities (14) from row to row, two "Chevron row" channels (15), two "Diamond" channels (16), and the spacing between the medial teeth (17).] These channels (15,16) function to aid further in the removal of bone chips and debris from the femoral canal upon broaching.

Preferably, most of the surface area of the broach comprises cutting teeth, which as shown in the figures and discussed herein, are positioned on all four faces of the broach. In addition, the entire distal end (30) of the inventive broach comprises no cutting teeth, and thus is preferably left substantially blank, as shown in FIGS. 1–3, for the attachment of a modular tip (not shown). Alternatively, cutting teeth could be positioned on the entire surface of the broach, including the distal end.

As already discussed above, the foregoing description of the preferred embodiments of the inventive broach was based largely in part on studies relating to the femoral anatomy and effect of cutting tooth design on broaching efficiency and gap formation (see Examples 1 and 2). It is conceivable, however, that variations in individual anatomy of the femoral cavity may necessitate variations in the types and positioning of the cutting teeth on the broach that are obvious to one of ordinary skill in the art, and therefore fall within the scope of the appended claims even though such variations were not specifically discussed above.

EXAMPLE 1

Effect of Broach Tooth Design on the Shape of the Femoral Cavity:

A study was conducted to evaluate the effect of cutting tooth design on the shape of the femoral cavity. Femoral broaches, each comprising teeth of only one of three different cutting tooth configurations were fabricated in 17-4 precipitation hardened stainless steel (Howmedica). All three broaches were of the identical external geometry and differed only in the design of cutting teeth. The first design (i.e. the "Standard" tooth) had cutting teeth with a rake angle of 0° and a relief angle of 25° oriented at right angles to the femoral axis. The second design (i.e. the "Diamond" tooth) consisted of coarse 6.35 mm Diamond-shaped teeth with a rake angle of $-10°$ and a relief angle of 40°. The third design (i.e. the "Chevron" tooth) consisted of parallel rows of teeth with a rake angle of 30° and a relief angle of 25°. Each row of teeth for the third design was angled at 60° to the cutting direction in a chevron pattern about the midline of the broach.

Nine embalmed cadaveric femora were prepared for implantation of cementless prosthesis using standard surgical techniques. After flexible reaming, a broach was inserted into a canal to the level of the femoral neck osteotomy. The broach was then removed and replaced with a precise cast metal replica of itself. The replica/bone interface was filled with low viscosity acrylic bone cement and permitted to cure. Each femur was then sectioned transversely and longitudinally into 6 mm slices to enable visualization of the replica/bone interface through stereo-microscopy.

Separation of the broach and the femoral cavity was measured at eight points around the circumference of each slice. Data from each broach design were analyzed and plotted using commercial software to generate a contour map of the distribution of gaps over the surface of each instrument (FIGS. 10–17).

The width of the bone/broach gaps varied from point to point within the femur. Overall, the largest gaps were present over the medial aspect of the broach in an arc which extended from its posterior to anterior surfaces. The width of all gaps decreased dramatically below the level of the femoral neck osteotomy and appeared to be directly related to the slope of the surface of the broach with respect to the femoral axis.

The gaps around the Standard broach ($0.12\pm0.2$ mm, range 0.0–0.47 mm), were significantly smaller than those generated by the Diamond ($0.26\pm0.04$ mm, range 0–1.01mm) ($p<0.0001$), and the Chevron ($0.37\pm0.04$ mm, range: 0.0–1.19 mm) ($p<0.0001$) designs. There was also a significant difference between the average gap width of the Chevron and the Diamond designs ($p<0.001$).

Significant gaps, defined as those larger than 0.5 mm, were not observed in any of the femora machined by the Standard broach, but appeared over $20\pm2.6\%$ of the measured surface of the Diamond broach, and over $28\pm6.4\%$ of the Chevron broach.

There was also a major difference between the three broach designs in terms of their ease of insertion into the femur. The Diamond broach required the least implantation force, followed by the Chevron and Standard designs.

EXAMPLE 2

Machining characteristics of femoral broaches with different cutting tooth designs:

An experimental apparatus was developed to allow a block of cancellous bone to be machined by a reciprocating broach under controlled conditions. The broach was attached to the actuator of a mechanical testing machine and cyclically displaced in an axial direction (amplitude: $\pm10$ mm, frequency: 1 cycle/second). A bone specimen was secured to a linear sliding platform which allowed the bone to move freely in a direction perpendicular to the axis of the broach during loading. A constant force of 220N (50 lb) was maintained normal to the broach/bone interface during each experiment. The displacement of the specimen was continuously monitored with a linear variable displacement transducer. The travel of the bone specimen and the broach, and the applied axial load, were continuously sampled at 95 Hz (Data Translation, MTS). All tests were performed under continuous saline irrigation to minimize heating effects.

Blocks of bovine cancellous bone measuring 50×25×25 mm were harvested from the distal femur and the proximal humerus. Each block was cut so that the broaching occurred in a plane parallel to the axis of the medullary canal. Prior to testing, high resolution radiographs were prepared to verify the uniformity of the cancellous bone in each specimen. The density of each specimen was also determined by weighing in air and distilled water. Specimens with a wet density of 1.15–1.25 gm/cm$^3$ were selected for testing.

Three designs of broaches were fabricated as described in Example 1. Each broach was supplied in the as-machined state and had no signs of apparent wear. The machining rate was calculated from the rate of lateral displacement of the bone specimen per axial cycle. To allow for the effect of accumulation of bone debris within the teeth of each broach, the initial and terminal machining rates were calculated at the fifth and twenty-fifth cycle of broach motion, respectively. The mechanical efficiency of each broach was also calculated from the tangential cutting force, the rate of bone removal, and the total distance traveled by the broach in contact with the bone specimen. In order to allow direct comparison of the three designs, all broaches were tested using four different bone specimens, using a "round robin" experimental design (Table 1):

TABLE 1

| TEST | BROACH ORDER |
|------|--------------|
| 1 | STANDARD, DIAMOND, CHEVRON |
| 2 | CHEVRON, STANDARD, DIAMOND |
| 3 | DIAMOND, CHEVRON, STANDARD |
| 4 | STANDARD, CHEVRON, STANDARD |

The rate of machining varied dramatically with the tooth design of each broaching instrument. There was no significant difference between the Diamond and Chevron designs in terms of initial or terminal machining rate or efficiency of machining. Both designs removed bone more that the rate of the rate of the Standard broach at the start of machining (p<0.0001) and six times the rate of the Standard broach once the cutting teeth had become packed with bone debris (p<0.0001).

There were large differences between the force required to machine bone using the three broach designs (Table 2). Under the conditions evaluated, the improved machining rate of the Chevron broach came with an almost two-fold increase in the force needed to move the broach in contact with the bone. This was in contrast to the Diamond design which only required 31% more force that the Standard design. In terms of the overall work of machining, the most efficient instrument was the Diamond broach which required 60% less energy that the Standard design per millimeter of bone removed. Similarly, the Chevron broach provided a 47% reduction compared to the Standard design.

TABLE 2

LOAD AND WORK PARAMETERS FOR EACH OF THE THREE DESIGNS

| BROACH | AXIAL LOAD (lbs) | MACHINING RATE (mcm**/cycle) | WORK OF* MACHINING (mJ/mcm**) |
|--------|------------------|------------------------------|-------------------------------|
| STANDARD | 106 +/– 6.9 (100%)*** | 103 +/– 17 (100%) | 45.0 (100%) |
| DIAMOND | 139 +/– 10.3 (131%) | 341 +/– 19 (331%) | 17.9 (40%) |
| CHEVRON | 206 +/– 4.4 (194%) | 388 +/– 62 (377%) | 23.8 (53%) |

*Work of Machining = $\frac{\text{Axial Force} \times \text{Machining Distance}}{\text{Rate of Machining}}$

**mcm = micrometers of bone

***All percentage values in parentheses are normalized with respect to the value recorded using the Standard broach

We claim:

1. A broach suitable for preparing an intramedullary canal of a bone for receiving a prosthetic stem, said broach comprising:
   (a) a longitudinal axis;
   (b) an anterior face, a posterior face, a medial face, and a lateral face generally corresponding in shape to the respective anterior, posterior, medial, and lateral faces of a prepared intramedullary canal; and
   (c) a plurality of cutting teeth having at least two different tooth configurations, wherein said plurality of teeth include a first set of teeth positioned on said lateral face and a second set of teeth positioned on at least one of said anterior and posterior faces, wherein each tooth of said first set of teeth has a different configuration from each tooth of said second set of teeth, and wherein said first set of teeth comprises at least one substantially pyramid-shaped tooth.

2. The broach of claim 1, wherein at least one of said first set of teeth has at least two cutting edges.

3. The broach of claim 2, wherein said first set of teeth comprises at least one substantially pyramid-shaped tooth.

4. The broach of claim 3, wherein said pyramid-shaped tooth has a relief angle of from about 20 degrees to about 60 degree and a rake angle of from about −10 degrees to about −40 degrees.

5. The broach of claim 4, wherein at least one substantially pyramid-shaped tooth has a substantially flat top portion.

6. The broach or claim 1, wherein at least one of said first set of teeth has at least three cutting edges, a relief angle of from about 15 degrees to about 60 degrees, and a rake angle of from about −10 degrees to about 20 degrees.

7. The broach of claim 2, wherein at least one of said second set of teeth has at least three cutting edges, a relief angle of from about 15 degrees to about 60 degrees, and a rake angle of from about −10 degrees to about 10 degrees.

8. The broach of claim 7, wherein said second set of teeth are positioned on one of said anterior and posterior faces in parallel rows, wherein said rows are positioned at a diagonal angle relative to the longitudinal axis of the broach.

9. The broach of claim 8, wherein each of said rows includes at least one concavity positioned between adjacent teeth of said row.

10. A broach suitable for preparing an intramedullary canal of a bone for receiving a prosthetic stem, said broach comprising a longitudinal axis and anterior, posterior, medial, and lateral faces, and wherein said broach further comprises a plurality of cutting teeth having at least three different tooth configurations positioned on one or more of said faces.

11. The broach of claim 10, wherein said plurality of cutting teeth comprises at least one tooth having at least two cutting edges.

12. The broach of claim 11, wherein said tooth is substantially pyramid-shaped.

13. The broach of claim 11, wherein said tooth has at least three cutting edges, a relief angle of from about 15 degrees to about 60 degrees, and a rake angle of from about −10 degrees to about 20 degrees.

14. The broach of claim 13, wherein a plurality of said teeth are positioned in parallel rows on at least one of said anterior and posterior faces at a diagonal angle relative to said longitudinal axis of said broach.

15. The broach of claim 14, wherein each of said rows of teeth include at least one concavity positioned between adjacent teeth.

16. The broach of claim 10, wherein said plurality of cutting teeth includes at least one tooth having a single cutting edge.

17. The broach of claim 16, wherein said tooth is positioned on said medial face of said broach.

18. The broach of claim 16, wherein said tooth has a relief angle of from about 0 to about 60 degrees and a rake angle of from about −10 to about 10 degrees.

19. The broach of claim 10, wherein said plurality of cutting teeth comprises at least three sets of tooth configurations, wherein said lateral face comprises a first set of teeth of one configuration positioned thereon, said medial face comprises a second set of teeth of a second configuration positioned thereon, and at least one of said remaining faces comprises a third set of teeth of a third configuration positioned thereon.

20. The broach of claim 19, wherein said first set of teeth comprises teeth having at least two cutting edges.

21. The broach of claim 20, wherein said first set of teeth includes a substantially pyramid-shaped tooth.

22. The broach of claim 20, wherein said first set of teeth include teeth each having at least three cutting edges, a rake angle of from about −10 degrees to about 20 degrees, and a relief angle of from about 15 to about 60 degrees.

23. The broach of claim 19, wherein said second set of teeth comprise a single cutting edge, a rake angle from about −10 degrees to about 10 degrees, and a relief angle of from about 0 degrees to about 60 degrees.

24. The broach of claim 19, wherein said third set of teeth are positioned in parallel rows at a diagonal angle relative to the longitudinal axis.

25. The broach of claim 24, wherein each tooth of said third set of teeth has at least three cutting edges, a relief angle from about 15 degrees to about 60 degrees, and a rake angle of from about −10 degrees to about 10 degrees.

26. The broach of claim 25, wherein each of said rows includes a concavity positioned between adjacent teeth of said row.

27. A broach suitable for preparing an intramedullary canal of a bone for receiving a prosthetic stem, said broach including a longitudinal axis and anterior, posterior, medial, and lateral faces, and wherein said broach further comprises:

(a) a first plurality of teeth positioned on said lateral face, wherein at least one of said first plurality of teeth is substantially pyramid-shaped;

(b) a second plurality of teeth positioned on said medial face, wherein at least one of said second plurality of teeth comprises a single cutting edge, a rake angle of from about −10 degrees to about 10 degrees, and a relief angle of from about 0 degrees to about 60 degrees; and (c) a third plurality of teeth positioned in parallel rows on said anterior and posterior faces at a diagonal angle relative to the longitudinal axis, wherein each of said third plurality of teeth has a rake angle of from about −10 degrees to about 10 degrees, and a relief angle of about 15 degrees to about 60 degrees.

28. The broach of claim 27, wherein each of said rows of teeth further comprises a concavity positioned between adjacent teeth of said row.

29. The broach of claim 27, wherein at least one of said substantially pyramid-shaped teeth has a substantially flat top.

* * * * *